United States Patent

Gomes et al.

Patent Number: 5,417,891
Date of Patent: May 23, 1995

[54] HIGH FOAMING NONIONIC SURFACTANT BASED LIQUID DETERGENT

[75] Inventors: Gilbert S. Gomes, Somerset, N.J.; Rita Erilli, Rocourt, Belgium; Stephen Repenic, Flemington, N.J.

[73] Assignee: Colgate Palmolive Co., Piscataway, N.J.

[21] Appl. No.: 91,511

[22] Filed: Jul. 9, 1993

Related U.S. Application Data

[63] Continuation-in-part of Ser. No. 893,138, Jun. 3, 1992, abandoned.

[51] Int. Cl.⁶ .............................................. C11D 1/83
[52] U.S. Cl. .................................. 252/552; 252/550; 252/551; 252/554; 252/173; 252/174.17; 252/174.21; 252/174.22; 252/DIG. 14
[58] Field of Search ............. 252/549, 550, 552, 554, 252/551, 558, 173, 174.17, 174.21, 174.22, 380, DIG. 14

[56] References Cited

U.S. PATENT DOCUMENTS

| | | | |
|---|---|---|---|
| 4,076,800 | 2/1978 | Marsh et al. | 424/70 |
| 4,671,895 | 6/1987 | Erilli et al. | 252/552 |
| 5,073,292 | 12/1991 | Hessel et al. | 252/174.12 |
| 5,190,747 | 3/1993 | Sekiguchi et al. | 424/56 |
| 5,244,593 | 9/1993 | Roselle et al. | 252/99 |

*Primary Examiner*—Paul Lieberman
*Assistant Examiner*—Lorna M. Douyon
*Attorney, Agent, or Firm*—Richard E. Nanfeldt; Robert C. Sullivan; Murray Grill

[57] ABSTRACT

A high foaming, light duty, liquid detergent with desirable cleansing properties and mildness to the human skin comprising four essential surfactants: a water soluble nonionic surfactant, a $C_{8-18}$ ethoxylated alkyl ether sulfate anionic surfactant a $C_{10}$–$C_{20}$ paraffin sodium sulfonate surfactant, a $C_8$–$C_{18}$ alcohol sulfate surfactant and the balance being water.

3 Claims, No Drawings

HIGH FOAMING NONIONIC SURFACTANT BASED LIQUID DETERGENT

RELATED APPLICATION

This application is a Continuation-in-part application of U.S. Ser. No. 07/893,138 filed June 3, 1992 now abandoned.

BACKGROUND OF THE INVENTION

The present invention relates to novel light duty liquid detergent compositions with high foaming properties, containing a nonionic surfactant, a sulfonate surfactant, an alcohol sulfate, and an ethoxylated alkyl ether sulfate surfactant, wherein the surfactants are dissolved in an aqueous medium.

Nonionic surfactants are in general chemically inert and stable toward pH change and are therefore well suited for mixing and formulation with other materials. The superior performance of nonionic surfactants on the removal of oily soil is well recognized. Nonionic surfactants are also known to be mild to human skin. However, as a class, nonionic surfactants are known to be low or moderate foamers. Consequently, for detergents which require copious and stable foam, the application of nonionic surfactants is limited. There have been substantial interest and efforts to develop a high foaming detergent with nonionic surfactants as the major active ingredient. Yet, little has been achieved.

The prior art is replete with light duty liquid detergent compositions containing nonionic surfactants in combination with anionic and/or betaine surfactants wherein the nonionic detergent is not the major active surfactant, as shown in U.S. Pat. No. 3,658,985 wherein an anionic based shampoo contains a minor amount of a fatty acid alkanolamide. U.S. Pat. No. 3,769,398 discloses a betaine-based shampoo containing minor amounts of nonionic surfactants. This patent states that the low foaming properties of nonionic detergents renders its use in shampoo compositions non-preferred. U.S. Pat. No. 4,329,335 also discloses a shampoo containing a betaine surfactant as the major ingredient and minor amounts of a nonionic surfactant and of a fatty acid mono- or di-ethanolamide. U.S. Pat. No. 4,259,204 discloses a shampoo comprising 0.8–20% by weight of an anionic phosphoric acid ester and one additional surfactant which may be either anionic, amphoteric, or nonionic. U.S. Pat. No. 4,329,334 discloses an anionic-amphoteric based shampoo containing a major amount of anionic surfactant and lesser amounts of a betaine and nonionic surfactants.

U.S. Pat. No. 3,935,129 discloses a liquid cleaning composition based on the alkali metal silicate content and containing five basic ingredients, namely, urea, glycerin, triethanolamine, an anionic detergent and a nonionic detergent. The silicate content determines the amount of anionic and/or nonionic detergent in the liquid cleaning composition. However, the foaming property of these detergent compositions is not discussed therein.

U.S. Pat. No. 4,129,515 discloses a heavy duty liquid detergent for laundering fabrics comprising a mixture of substantially equal amounts of anionic and nonionic surfactants, alkanolamines and magnesium salts, and, optionally, zwitterionic surfactants as suds modifiers.

U.S. Pat. No. 4,224,195 discloses an aqueous detergent composition for laundering socks or stockings comprising a specific group of nonionic detergents, namely, an ethylene oxide of a secondary alcohol, a specific group of anionic detergents, namely, a sulfuric ester salt of an ethylene oxide adduct of a secondary alcohol, and an amphoteric surfactant which may be a betaine, wherein either the anionic or nonionic surfactant may be the major ingredient.

The prior art also discloses detergent compositions containing all nonionic surfactants as shown in U.S. Pat. Nos. 4,154,706 and 4,329,336 wherein the shampoo compositions contain a plurality of particular nonionic surfactants in order to effect desirable foaming and detersive properties despite the fact that nonionic surfactants are usually deficient in such properties.

U.S. Pat. No. 4,013,787 discloses a piperazine based polymer in conditioning and shampoo compositions which may contain all nonionic surfactant or all anionic surfactant.

U.S. Pat. 4,671,895 teaches a liquid detergent composition containing an alcohol sulfate surfactant, a nonionic surfactant, a paraffin sulfonate surfactant, an alkyl ether sulfate surfactant and water but fails to disclose an alkyl polysaccharide surfactant.

U.S. Pat. No. 4,450,091 discloses high viscosity shampoo compositions containing a blend of an amphoteric betaine surfactant, a potyoxybutylene polyoxyethylene nonionic detergent, an anionic surfactant, a fatty acid alkanolamide and a polyoxyalkylene glycol fatty ester. But, none of the exemplified compositions contains an active ingredient mixture wherein the nonionic detergent is present in major proportion, probably due to the low foaming properties of the polyoxybutylene polyoxyethylene nonionic detergent.

U.S. Pat. No. 4,595,526 describes a composition comprising a nonionic surfactant, a betaine surfactant, an anionic surfactant and a $C_{12}$–$C_{14}$ fatty acid monethanolamide foam stabilizer.

However, none of the above-cited patents discloses a high foaming, liquid detergent composition containing a nonionic surfactant, a supplementary high foaming anionic sulfonate surfactant, an alcohol sulfate surfactant, and an ethoxylated alkylether sulfate surfactant as the four essential ingredients, and the composition does not contain any HEDTA, amine oxide, alkanolamides, clays, abrasives, silicas, clay or polymeric thickeners, alkaline earth metal carbonates, alkyl glycine surfactant, cyclic imidinium surfactant, alkali metal carbonates or more than 3 wt % of a fatty acid or its salt thereof.

SUMMARY OF THE INVENTION

It has now been found that a high foaming liquid detergent can be formulated with a nonionic surfactant which has desirable cleaning properties, mildness to the human skin.

An object of this invention is to provide novel, liquid detergent composition containing a nonionic surfactant, an anionic alcohol sulfate surfactant, a sulfonate surfactant and an ethoxylated alkyl ether sulfate surfactant, wherein the composition does not contain any amine oxide, HEDTA, fatty acid alkanolamides, clays, silicas, abrasives, clay or polymeric thickeners, alkali metal carbonates, alkaline earth metal carbonates, clay or polymeric thickener, alkyl glycine surfactant, cyclic imidinium surfactant, or more than 3 wt. % of a fatty acid or salt thereof.

Another object of this invention is to provide a novel, liquid detergent with desirable high foaming and cleaning properties which is mild to the human skin.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentatities and combinations particularly pointed out in the appended claims.

To achieve the foregoing and other objects and in accordance with the purpose of the present invention, as embodied and broadly described herein the novel, high foaming, light duty liquid detergent of this invention comprises four essential surfactants: a water soluble, ethoxylated, nonionic surfactant, a foaming anionic sulfate surfactant, an ethoxylated alkyl ether sulfate surfactant and a sulfonate anionic surfactant, wherein the surfactants are dissolved in an aqueous vehicle wherein the composition does not contain any amine oxide, HEDTA, fatty acid alkanolamides, clays, silicas, abrasives, clay or polymeric thickeners, alkali metal carbonates, alkaline earth metal carbonates, clay or polymeric thickener, alkyl glycine surfactant, cyclic imidinium surfactant or more than 3 wt. % of a fatty acid or salt thereof.

More specifically, the present invention relates to a high foaming, liquid detergent containing a nonionic surfactant selected from the group consisting of water soluble primary aliphatic alcohol ethoxylates secondary aliphatic alcohol ethoxylates, alkyl phenol ethoxylates and alcohol ethylene oxide propylene oxide condensates; an alcohol sulfate anionic surfactant, a water soluble salts of C8–C16 sulfonate surfactant and an ethoxylated alkyl ether sulfate surfactant.

DETAILED DESCRIPTION OF THE INVENTION

The high foaming nonionic based light duty liquid detergent compositions of the instant invention comprise approximately by weight: 1 to 10 wt. % of a water soluble nonionic surfactant; 0.5 to 6 wt. % of a water soluble or dispersible alcohol sulfate anionic surfactant; 1 to 8% of an ethoxylated alkyl ether sulfate surfactant and 20 to 40% of an anionic sulfonate surfactant; the balance being water, wherein the compositions do not contain any amine oxides, fatty acid alkanol amides (for example—cocodiethanol amide), formate, calcium carbonate, clay or polymeric thickeners, abrasives, clays, silicas, alkyl glycine surfactant, cyclic imidinium surfactant, or more than 3 wt % of a fatty acid or a metal salt of the fatty acid.

The nonionic surfactant is present in amounts of about 1 to 10%, preferably 2 to 9% by weight of the composition and provides superior performance in the removal of oily soil and mildness to human skin.

The water soluble nonionic surfactants utilized in this invention are commercially well known and include the primary aliphatic alcohol ethoxylates, secondary aliphatic alcohol ethoxylates, alkylphenol ethoxylates and ethylene-oxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic detergent class includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9–15 carbon atoms, such as C$_9$–C$_{11}$ alkanol condensed with 7 to 10 moles of ethylene oxide (Neodol 91-8), C$_{12-13}$ alkanol condensed with 6.5 moles ethylene oxide (Neodol 23-6.5), C$_{12-15}$ alkanol condensed with 12 moles ethylene oxide (Neodol 25-12), C$_{14-15}$ alkanol condensed with 13 moles ethylene oxide (Neodol 45-13), and the like. Such ethoxamers have an HLB (hydrophobic lipophilic balance) value of about 8 to 15 and give good O/W emulsification, whereas ethoxamers with HLB values below 8 contain less than 5 ethyleneoxide groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are C$_{11}$–C$_{15}$ secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of EO per mole of nonyl phenol, dinonyl phenol condensed with about 12 moles of EO per mole of phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

Also among the satisfactory nonionic detergents are the water-soluble condensation products of a C$_8$–C$_{20}$ alkanol with a hereric mixture of ethylene oxide and propylene oxide wherein the weight ratio of ethylene oxide to propylene oxide is from 2.5:1 to 4:1, preferably 2.8:1 to 3.3:1, with the total of the ethylene oxide and propylene oxide (including the terminal ethanol or propanol group) being from 60–85%, preferably 70–80%, by weight. Such detergents are commercially available from BASF-Wyandotte and a particularly preferred detergent is a $C_{10}$–$C_{16}$ alkanol condensate with ethylene oxide and propylene oxide, the weight ratio of ethylene oxide to propylene oxide being 3:1 and the total alkoxy content being about 75% by weight.

Condensates of 2 to 30 moles of ethylene oxide with sorbitan mono- and tri-$C_{10}$–$C_{20}$ alkanoic acid esters having a HLB of 8 to 15 also may be employed as the nonionic detergent ingredient in the described composition. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

Other suitable water-soluble nonionic detergents which are less preferred are marketed under the trade name "Pluronics." The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L 62 and L 64.

The anionic alcohol sulfate and sulfonate surfactants which may be used in the detergent of this invention are water soluble such as triethanolamine and include the sodium, potassium, ammonium and ethanolammonium salts of $C_8$–$C_{18}$ alkyl sulfates such as lauryl sulfate, myristyl sulfate and the like; linear $C_8$–$C_{16}$ alkyl benzene sulfonates; $C_{10}$–$C_{20}$ paraffin sulfonates and alpha olefin sulfonates containing about 10–24 carbon atoms. The preferred alcohol sulfate surfactant is a $C_8$ to $C_{10}$ alcohol sulfate and is present in the composition at a concentration of about 0.5 to 6 wt. % and the preferred anionic sulfonate surfactant is a $C_{10-20}$ paraffin sulfonate present in the composition at a concentration of about 20 to 40 wt. %.

The paraffin sulfonates may be monosulfonates or di-sulfonates and usually are mixtures thereof, obtained by sulfonating paraffins of 10 to 20 carbon atoms. Preferred paraffin sulfonates are those of $C_{12-18}$ carbon atoms chains, and more preferably they are of $C_{14-17}$ chains. Paraffin sulfonates that have the sulfonate group(s) distributed along the paraffin chain are described in U.S. Pat. Nos. 2,503,280; 2,507,088; 3,260,744; and 3,372,188; and also in German Patent 735,096. Such compounds may be made to specifications and desirably the content of paraffin sulfonates outside the $C_{14-17}$ range will be minor and will be minimized, as will be any contents of di- or poly-sulfonates.

Examples of suitable other sulfonated anionic detergents are the well known higher alkyl mononuclear aromatic sulfonates, such as the higher alkylbenzene sulfonates containing 9 to 18 or preferably 9 to 10 to 15 or 16 carbon atoms in the higher alkyl group in a straight or branched chain, or C8–15 alkyl toulene sulfonates. A preferred alkylbenzene sulfonate is a linear alkylbenzene sulfonate having a higher content of 3-phenyl (or higher) isomers and a correspondingly lower content (well below 50%) of 2-phenyl (or lower) isomers, such as those sulfonates wherein the benzene ring is attached mostly at the 3 or higher (for example 4, 5, 6 or 7) position of the alkyl group and the content of the isomers in which the benzene ring is attached in the 2 or 1 position is correspondingly low. Preferred materials are set forth in U.S. Pat. No. 3,320,174, especially those in which the alkyls are of 10 to 13 carbon atoms.

The C8-18 ethoxylated alkyl ether sulfate surfactants have the structure

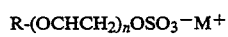

$$R\text{-}(OCHCH_2)_n OSO_3^- M^+$$

wherein n is about 1 to about 22 more preferably 1 to 3 and R is an alkyl group having about 8 to about 18 carbon atoms, more preferably 12 to 15 and natural cuts, for example, $C_{12-14}$; $C_{12-15}$ and M is an ammonium cation or a metal cation, most preferably sodium. The solubilizing agent is present in the composition at a concentration of about 0.5 to about 8.0 wt. %, more preferably about 1.0 to 7.0 wt. %.

The ethoxylated alkyl ether sulfate may be made by sulfating the condensation product of ethylene oxide and $C_{8-10}$ alkanol, and neutralizing the resultant product. The ethoxylated alkyl ether sulfates differ from one another in the number of carbon atoms in the alcohols and in the number of moles of ethylene oxide reacted with one mole of such alcohol. Preferred ethoxylated alkyl ether polyethenoxy sulfates contain 12 to 15 carbon atoms in the alcohols and in the alkyl groups thereof, e.g., sodium myristyl (3 EO) sulfate.

Ethoxylated $C_{8-18}$ alkylphenyl ether sulfates containing from 2 to 6 moles of ethylene oxide in the molecule also are suitable for use in the invention compositions. These detergents can be prepared by reacting an alkyl phenol with 2 to 6 moles of ethylene oxide and sulfating and neutralizing the resultant ethoxylated alkylphenol. The concentration of the ethoxylated alkyl ether sulfate surfactant is about 1 to about 8 wt. %.

The instant compositions contains about 1 to about 4 wt. %, more preferably about 0.5 to 3 wt. % of an alkyl polysaccharide surfactant as a foam enhancer. The alkyl polysaccharides surfactants, which are used in conjunction with the aforementioned surfactant have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4- positions rather than at the 1-position, (thus giving e.g. a glucosyl or galactosyl as opposed to a glucoside or galactoside). However, attachment through the 1- position, i.e., glucosides, galactoside, fructosides, etc., is preferred. In the preferred product the additional saccharide units are predominately attached to the previous saccharide unit's 2-position. Attachment through the 3-, 4-, and 6- positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula $$R_2O(C_nH_{2n}O)_r(Z)_x$$

wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferable 0; and x is from 1.5 to 8, preferably from 1.5 to 4, most preferably from 1.6 to 2.7. To prepare these compounds a long chain alcohol (R$_2$OH) can be reacted with glucose, in the presence of an acid catalyst to form the desired glucoside. Alternatively the alkyl polyglucosides can be prepared by a two step procedure in which a short chain alcohol (R$_1$OH) can be reacted with glucose, in the presence of an acid catalyst to form the desired glucoside. Alternatively the alkyl polyglucosides can be prepared by a two step procedure in which a short chain alcohol (C$_{1-6}$) is reacted with glucose or a polyglucoside (x=2 to 4) to yield a short chain alkyl glucoside (x=1 to 4) which can in turn be reacted with a longer chain alcohol (R$_2$OH) to displace the short chain alcohol and obtain the desired alkyl polyglucoside. If this two step procedure is used, the short chain alkylglucoside content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is APG 625 glycoside manufactured by the Henkel Corporation of Ambler, Pa. APG25 is a nonionic alkyl polyglycoside characterized by the formula:

$$C_nH_{2n+1}O(C_6H_{10}O_5)_xH$$

wherein n=10 (2%); n=122 (65%); n=14 (21–28%); n=16 (4–8%) and n=18 (0.5%) and x (degree of polymerization)=1.6. APG 625 has: a pH of 6 to 10 (10% of APG 625 in distilled water); a specific gravity at 25° C. of 1.1 g/ml; a density at 25° C. of 9.1 lbs/gallon; a calculated HLB of 12.1 and a Brookfield viscosity at 35° C., 21 spindle, 5–10 RPM of 3,000 to 7,000 cps.

The instant compositions can contain a silk derivatives as part of the composition and generally constitute about 0.01 to 3.0% by weight, preferably about 0.1 to 3.0% by weight, most preferably 0.2 to 2.5% by weight of the liquid detergent composition.

Included among the silk derivatives are silk fibers and hydrolyzate of silk fibers. The silk fibers may be used in the form of powder in preparing the liquid detergent or as a powder of a product obtained by washing and treating the silk fibers with an acid. Preferably, silk fibers are used as a product obtained by hydrolysis with an acid, alkali or enzyme, as disclosed in Yoshiaki Abe et al., U.S. Pat. No. 4,839,168; Taichi Watanube et al., U.S. Pat. No. 5,009,813; and Marvin E. Goldberg, U.S. Pat. No. 5,069,898, each incorporated herein by reference.

Another silk derivative which may be employed in the composition of the present invention is protein obtained from degumming raw silk, as disclosed, for example, in Udo Hoppe et al., U.S. Pat. No. 4,839,165, incorporated herein by reference. The principal protein obtained from the raw silk is sericin which has an empirical formula of $C_{15}H_{25}O_3N_5$ and a molecular weight of 323.5.

Another example of a silk derivative for use in the liquid detergent composition of the present invention is a fine powder of silk fibroin in nonfibrous or particulate form, as disclosed in Kiyoshi Otoi et al., U.S. Pat. No. 4,233,212, incorporated herein by reference.

The fine powder is produced by dissolving a degummed silk material in at least one solvent selected from, for example, an aqueous cupriethylene diamine solution, an aqueous ammoniacal solution of cupric hydroxide, an aqueous alkaline solution of cupric hydroxide and glycerol, an aqueous lithium bromide solution, an aqueous solution of the chloride, nitrate or thiocyanate of calcium, magnesium or zinc and an aqueous sodium thiocyanate solution. The resulting fibroin solution is then dialyzed. The dialyzed aqueous silk fibroin solution, having a silk fibroin concentration of from about 3 to 20% by weight, is subjected to at least one treatment for coagulating and precipitating the silk fibroin, such as, for example, by the addition of a coagulating salt, by aeration, by coagulation at the isoelectric point, by exposure to ultrasonic waves, by agitation at high shear rate and the like.

The resulting product is a silk fibroin gel which may be incorporated directly into the liquid detergent composition or the same may be dehydrated and dried into a powder and then dissolved in the liquid detergent composition.

The silk material which may be used to form the silk fibroin includes cocoons, raw silk, waste cocoons, raw silk waste, silk fabric waste and the like. The silk material is degummed or freed from sericin by a conventional procedure such as, for example, by washing in warm water containing a surfact-active agent or an enzyme, and then dried. The degummed material is dissolved in the solvent and preheated to a temperature of from 60° to 95° C., preferably 70° to 85° C. Further details of the process of obtaining the silk fibroin are discussed in U.S. Pat. No. 4,233,212.

A preferred silk derivative is a mixture of two or more individual amino acids which naturally occur in silk. The principal silk amino acids are glycine, alanine, serine and tyrosine.

A silk amino acid mixture resulting from the hydrolysis of silk of low molecular weight and having a specific gravity of at least 1 is produced by Croda, Inc. and sold under the trade name "CROSILK LIQUID" which typically has a solids content in the range of about 27 to 31% by weight. Further details of the silk amino acid mixture can be found in Wendy W. Kim et al., U.S. Pat. No. 4,906,460, incorporated herein by reference. A typical amino acid composition of "CROSILK LIQUID" is shown in the following Table.

| AMINO ACID | PERCENT BY WEIGHT |
|---|---|
| Alanine | 28.4 |
| Glycine | 34.7 |
| Valine | 2.0 |
| Leucine | 1.2 |
| Proline | 1.2 |
| Tyrosine | 0.6 |
| Phenylalanine | 0.9 |
| Serine | 15.4 |
| Threonine | 1.9 |
| Arginine | 1.5 |
| Aspartic Acid | 4.7 |
| Glutamic Acid | 4.1 |
| Isoleucine | 0.8 |
| Lysine | 1.4 |
| Histidine | 0.8 |
| Cystine | 0.1 |
| Methionine | 0.2 |
| TOTAL | 99.9 |

The instant compositions can contain a viscosity modifying solvent at a concentration of about 0.1 to 5.0 weight percent, more preferably about 0.5 to 4.0 weight percent. The viscosity modifying agent is an alcohol of the formula

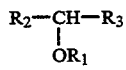

wherein $R_1 = CH_3$, $CH_2CH_3$ $R_2 = CH_3$, $CH_2CH_3$ $R_3 = CH_2OH$, $CH_2CH_2OH$; which is preferably 3-methyl-3-methoxy-butanol.

The 3-methyl-3-methoxy butanol is commercially available from Sattva Chemical Company of Stamford, Conn. and Kuraray Co., Ltd., Osaka, Japan.

The instant composition can contain about 0.1 to 4.0% of a protein selected from the group consisting of hydrolyzed animal collagen protein obtained by an enzymatic hydrolysis, vegetal protein and hydrolyzed wheat protein and mixtures thereof.

All of the aforesaid four ingredients in this light duty liquid detergent are water soluble or water dispersible and remain so during storage.

This particular combination of anionic alcohol sulfate surfactant, an anionic paraffin sulfonate surfactant and an anionic surfactant which is an alkali or ammonium metal salt of a $C_8$-$C_{18}$ ethoxylated alkyl ether sulfate surfactant provides a detergent system which coacts with the nonionic surfactant to produce a liquid detergent composition with desirable foaming, foam stability and detersive properties and mildness to human skin. Surprisingly, the resultant homogeneous liquid detergent exhibits the same or better foam performance, both as to initial foam volume and stability of foam in the presence of soils, and cleaning efficacy as an anionic based light duty liquid detergent (LDLD) as shown in the following Examples.

The essential ingredients discussed above are solubilized in an aqueous medium comprising water and optionally, solubilizing ingredients such as C2-C3 mono and di- hydroxy alkanols, e.g., ethanol, isopropanol and propylene glycol. Suitable water soluble hydrotropic salts include sodium, potassium, ammonium and mono-, di- and triethanolammonium salts. While the aqueous medium is primarily water, preferably said solubilizing agents are included in order to control the viscosity of the liquid composition and to control low temperature cloud clear properties. Usually, it is desirable to maintain clarity to a temperature in the range of 5° C. to 10° C. Therefore, the proportion of solubilizer generally will be from about 1% to 15%, preferably 2% to 12%, most preferably 3% to 8%, by weight of the detergent composition with the proportion of ethanol, when present, being 5% of weight or less in order to provide a composition having a flash point above about 46° C. Preferably the solubilizing ingredient will be a mixture of ethanol and either sodium xylene sulfonate or sodium cumene sulfonate or a mixture of said sulfonates or ethanol and urea. Inorganic salts such as sodium sulfate, magnesium sulfate, sodium chloride and sodium citrate can be added at concentrations of 0.5 to 8.0 wt. %, preferably 1 to 6 wt. % to modify the cloud point of the nonionic surfactant and thereby control the haze of the resultant solution. Various other ingredients such as urea at a concentration of about 0.5 to 4.0 wt. % or urea at the same concentration in combination with ethanol at a concentration of about 0.5 to 4.0 wt. % can be used as solubilizing agents. Another extremely effective solubilizing or cosolubilizing agent used at a concentration of about 0.1 to 5 wt. percent, more preferably about 0.5 to 4.0 weight percent is isethionic acid or an alkali metal salt of isethionic acid having the formula:

wherein X is hydrogen or an alkali metal cation, preferably sodium. Other ingredients which have been added to the compositions at concentrations of about 0.1 to 4.0 wt. percent are perfumes, sodium bisulfite, ETDA, isethionic and proteins such as lexeine protein.

The foregoing solubilizing ingredients also facilitate the manufacture of the inventive compositions because they tend to inhibit gel formation.

In addition to the previously mentioned essential and optional constituents of the light duty liquid detergent, one may also employ normal and conventional adjuvants, provided they do not adversely affect the properties of the detergent. Thus, there may be used various coloring agents and perfumes; ultraviolet light absorbers such as the Uvinuls, which are products of GAF Corporation; sequestering agents such as ethylene diamine tetraacetates; magnesium sulfate heptahydrate; pearlescing agents and opacifiers; pH modifiers; etc. The proportion of such adjuvant materials, in total will be about 1% to 15% of weight of the detergent composition, and the percentages of most of such individual components will be a maximum of 5% by weight and preferably less than about 2% by weight. Sodium formate can be included in the formula as a preservative at a concentration of 0.1 to 4.0%. Other preservatives are dibromodicyanobutane, citric acid, benzylic alcohol and poly (Hexamethylene) biguanidium hydrochloride and mixtures thereof. Sodium bisulfite can be used as a color stabilizer at a concentration of about 0.01 to 0.2 wt. %

The present light duty liquid detergents such as dishwashing liquids are readily made by simple mixing methods from readily available components which, on storage, do not adversely affect the entire composition. However, it is preferred that the nonionic surfactant be mixed with the solubilizing ingredients, e.g., ethanol and, if present, prior to the addition of the water to prevent possible gelation. The nonionic based surfactant system is prepared by sequentially adding with agitation the alkali metal salt of the $C_{8-18}$ ethoxylated alkyl ether sulfate, and then the alcohol sulfate surfactant and the paraffin sulfonate surfactant to the nonionic surfactant which has been previously optionally been mixed with a solubilizing agent such as ethyl alcohol and/or sodium xylene sulfonate to assist in solubilizing said surfactants, and then adding with agitation the formula amount of water to form an aqueous solution of the detergent composition. The use of mild heating (up to 100° C.) assists in the solubilization of the surfactants. The viscosities are adjustable by changing the total percentage of active ingredients. No polymeric or clay thickening agent is added. In all such cases the product made will be pourable from a relatively narrow mouth bottle (1.5 cm. diameter) or opening, and the viscosity of the detergent formulation will not be so low as to be like water. The viscosity of the detergent desirably will be at least 100 centipoises (cps) at room temperature, but may be up to about 1,000 centipoises as measured with a Brookfield Viscometer using a number 2 spindle rotating at 30 rpms. Its viscosity may approximate those of commercially acceptable detergents now on the market. The detergent viscosity and the detergent itself remain stable on storage for lengthy periods of time, without color changes or settling out of any insoluble materials. The pH of this formation is substantially neutral to skin, e.g., about 4.5 to 8 and preferably about 7.0.

These products have unexpectedly desirable properties. For example, the foam quality and detersive property is equal to or better than standard light duty liquid detergents while using a nonionic surfactant as the primary surfactant and minimal amounts of anionic surfactant, thereby achieving a less irritating liquid detergent than the standard light duty liquid detergent.

The following examples are merely illustrative of the invention and are not to be construed as limiting thereof.

DESCRIPTION OF THE PREFERRED EMBODIMENTS

EXAMPLE 1

The following formulas were prepared at room temperature by simple liquid mixing procedures as previously described.

|  | A |
|---|---|
| Nonionic Neodol 1-9 | 5.7 |
| Sodium Lauryl Ether Sulfate (AEOS) (2.0 EO) | 2.85 |
| Sodium C8-C10 Alcohol Sulfate | 0.95 |
| Perfume | 0.25 |
| Preservative KKM446 | 0.06 |
| Paraffin Sodium Sulfonate | 28.5 |
| Wheat protein |  |
| Lecithin Mactan FLC (Norte) | 0.5 |
| APG600 | 1.15 |
| Water | Balance |
| Appearance | Clear |
| Clear Point less than | 13° C. |
| Cloud Point less than | 0° C. |
| Brookfield Viscosity #2 spindle, 30 rpms cps | 250 |

A comparison of formula A to the commercially available Palmolive ™ light duty liquid detergent was made. Formula A had equal results to the Palmolive for a miniplate list as well as hand dishwashing test. Formula A exhibited superior foaming as compared to the commercial Palmolive product.

What is claimed is:

1. A high foaming light duty liquid detergent composition consisting of approximately by weight:
   (a) 1% to 10% of a water soluble nonionic surfactant selected from the group consisting of primary and secondary $C_8$–$C_{18}$ alkanol condensates with 5 to 30 moles of ethylene oxide, condensates of $C_8$–$C_{18}$ alkylphenol with 5 to 30 moles of ethylene oxide, condensates of $C_8$–$C_{20}$ alkanol with a heteric mixture of ethylene oxide and propylene oxide having a weight ratio of ethylene oxide to propylene oxide from 2.5:1 to 4:1 and a total alkylene oxide content to 60% to 85% by weight and condensates of 2 to 30 moles of ethylene oxide with sorbitan mono and tri-$C_{10}$–$C_{20}$ alkanoic acid esters having an HLB of 8 to 15;
   (b) 1% to 8% of a water-soluble ammonium or metal salt of a $C_8$–$C_{18}$ ethoxylated alkyl ether sulfate surfactant;
   (c) 20% to 40% of a water-soluble $C_{10}$–$C_{20}$ paraffin sulfonate surfactant;
   (d) 0.5% to 6% of a $C_8$–$C_{18}$ alcohol sulfate surfactant;
   (e) 1% to 4% of an alkyl polyglucoside surfactant having the formula $R_2O(C_nH_{2n}O)_r(Z)_x$ wherein Z is derived from glucose, R is selected from the group consisting of alkyl, alkyl phenyl and hydroxyalkylphenyl groups having 10 to 18 carbon atoms, n is 2 or 3, r is 0 to 10 and x is 1.5 to 8; and
   (f) the balance being water in which said nonionic surfactant, said polysaccharide surfactant, said $C_8$–$C_{18}$ ethyoxylated alkyl ether sulfate surfactant, said $C_{10}$–$C_{20}$ paraffin sulfonate surfactant and said $C_8$–$C_{18}$ alcohol sulfate surfactant are solubilized in said water, said composition does not contain any amine oxide and does not contain any alkanol amide.

2. A high foaming light duty liquid detergent composition consisting of approximately by weight:
   (a) 1% to 10% of a water soluble nonionic surfactant selected from the group consisting of primary and secondary $C_8$–$C_{18}$ alkanol condensates with 5 to 30 moles of ethylene oxide, condensates of $C_8$–$C_{18}$ alkylphenol with 5 to 30 moles of ethylene oxide, condensates of $C_8$–$C_{20}$ alkanol with a heteric mixture of ethylene oxide and propylene oxide having a weight ratio of ethylene oxide to propylene oxide from 2.5:1 to 4:1 and a total alkylene oxide content of 60% to 85% by weight and condensates of 2 to 30 moles of ethylene oxide with sorbitan mono and tri-$C_{10}$–$C_{20}$ alkanoic acid esters having an HLB of 8 to 15;
   (b) 1% to 8% of a water-soluble ammonium or metal salt of a $C_8$–$C_{18}$ ethoxylated alkyl ether sulfate surfactant;
   (c) 20% to 40% of a water-soluble $C_{10}$–$C_{20}$ paraffin sulfonate surfactant;
   (d) 0.5% to 6% of a $C_8$–$C_{18}$ alcohol sulfate surfactant;
   (e) 1% to 4% of an alkyl polyglucoside surfactant having the formula $$R_2O(C_nH_{2n}O)_r(Z)_x$$

wherein Z is derived from glucose, R is selected from the group consisting of alkyl, alkyl phenyl and hydroxyalkylphenyl groups having 10 to 18 carbon atoms, n is 2 or 3, r is 0 to 10 and x is 1.5 to 8;
   (f) 0.5% to 4.0% of isethionic acid or an alkali metal salt of isethionic acid; and
   (g) the balance being water in which said nonionic surfactant, said polysaccharide surfactant, said $C_8$–$C_{18}$ ethyoxylated alkyl ether solfate surfactant, said $C_{10}$–$C_{20}$ paraffin sulfonate surfactant and said $C_8$–$C_{18}$ alcohol solfate surfactant are solubilized in said water, said composition does not contain any amine oxide and does not contain any alkanol amide.

3. A high foaming light duty liquid detergent composition consisting of approximately by weight:
   (a) 1% to 10% of a water soluble nonionic surfactant selected from the group consisting of primary and secondary $C_8$–$C_{18}$ alkanol condensates with 5 to 30 moles of ethylene oxide, condensates of $C_8$–$C_{18}$ alkylphenol with 5 to 30 moles of ethylene oxide, condensates of $C_8$–$C_{20}$ alkanol with a heteric mixture of ethylene oxide and propylene oxide having a weight ratio of ethylene oxide to propylene oxide from 2.5:1 to 4:1 and a total alkylene oxide content of 60% to 85% by weight and condensates of 2 to 30 moles of ethylene oxide with sorbitan mono and tri-$C_{10}$–$C_{20}$ alkanoic acid esters having an HLB of 8 to 15;
   (b) 1% to 8% of a water-soluble ammonium or metal salt of a $C_8$–$C_{18}$ ethoxylated alkyl ether sulfate surfactant;
   (c) 20% to 40% of a water-soluble $C_{10}$–$C_{20}$ paraffin sulfonate surfactant;
   (d) 0.5% to 6% of a $C_8$–$C_{18}$ alcohol sulfate surfactant;
   (e) 1% to 4% of an alkyl polyglucoside surfactant having the formula $$R_2O(C_nH_{2n}O)_r(Z)_x$$

wherein Z is derived from glucose, R is selected from the group consisting of alkyl, alkyl phenyl and hydroxyalkylphenyl groups having 10 to 18 carbon atoms, n is 2 or 3, r is 0 to 10 and x is 1.5 to 8;
   (f) up to about 5% of ethanol or propylene glycol; and
   (g) the balance being water in which said nonionic surfactant, said polysaccharide surfactant, said $C_8$–$C_{18}$ ethyoxylated alkyl ether sulfate surfactant, said $C_{10}$–$C_{20}$ paraffin sulfonate surfactant and said $C_8$–$C_{18}$ alcohol sulfate surfactant are solubilized in said water, said composition does not contain any amine oxide and does not contain any alkanol amide.

* * * * *